(12) United States Patent
Bartfeld et al.

(10) Patent No.: US 9,031,853 B2
(45) Date of Patent: *May 12, 2015

(54) APPARATUS AND METHOD FOR OBTAINING AN IDENTIFICATION OF DRUGS FOR ENHANCED SAFETY

(75) Inventors: Eyal Bartfeld, Lexington, MA (US); Amir Lass, London (GB)

(73) Assignee: Irody, Inc., Boston, MA (US)

( * ) Notice: Subject to any disclaimer, the term of this patent is extended or adjusted under 35 U.S.C. 154(b) by 1749 days.

This patent is subject to a terminal disclaimer.

(21) Appl. No.: 11/744,869

(22) Filed: May 6, 2007

(65) Prior Publication Data

US 2007/0265880 A1     Nov. 15, 2007

Related U.S. Application Data

(60) Provisional application No. 60/798,278, filed on May 6, 2006, provisional application No. 60/798,279, filed on May 6, 2006.

(51) Int. Cl.
| | | |
|---|---|---|
| *G06Q 10/00* | (2012.01) | |
| *G06F 19/00* | (2011.01) | |
| *G06Q 40/08* | (2012.01) | |
| *G06Q 50/22* | (2012.01) | |
| *G06Q 50/24* | (2012.01) | |
| *G07F 17/00* | (2006.01) | |
| *G07G 1/00* | (2006.01) | |

(52) U.S. Cl.
CPC ............ *G06Q 10/00* (2013.01); *G06F 19/3462* (2013.01); *G06Q 40/08* (2013.01); *G06Q 50/22* (2013.01); *G06Q 50/24* (2013.01); *G07F 17/0092* (2013.01); *G07G 1/0054* (2013.01)

(58) Field of Classification Search
CPC ... G06Q 50/22; G01N 21/359; G06F 19/3462
USPC ......................................................... 705/2–3
See application file for complete search history.

(56) References Cited

U.S. PATENT DOCUMENTS

| | | | | |
|---|---|---|---|---|
| 4,759,074 A | * | 7/1988 | Iadipaolo et al. ............. | 382/152 |
| 6,294,999 B1 | * | 9/2001 | Yarin et al. .................. | 340/573.1 |
| 2006/0124656 A1 | * | 6/2006 | Popovich, Jr. .................... | 221/9 |

FOREIGN PATENT DOCUMENTS

WO      WO 02/081015      * 10/2002

* cited by examiner

*Primary Examiner* — Minnah Seoh
(74) *Attorney, Agent, or Firm* — Lawson & Weitzen, LLP; Sonia K. Guterman; Anna E. Stanford

(57) ABSTRACT

A device for identifying a drug, the device including at least one sensor for sensing and recording selected characteristics of a drug to be identified for compatibility with a pre-selected drug regimen, elements for transferring the recorded characteristics for analysis, elements for receiving analyzed data of the recorded characteristics, and a display for displaying the received data.

4 Claims, 12 Drawing Sheets

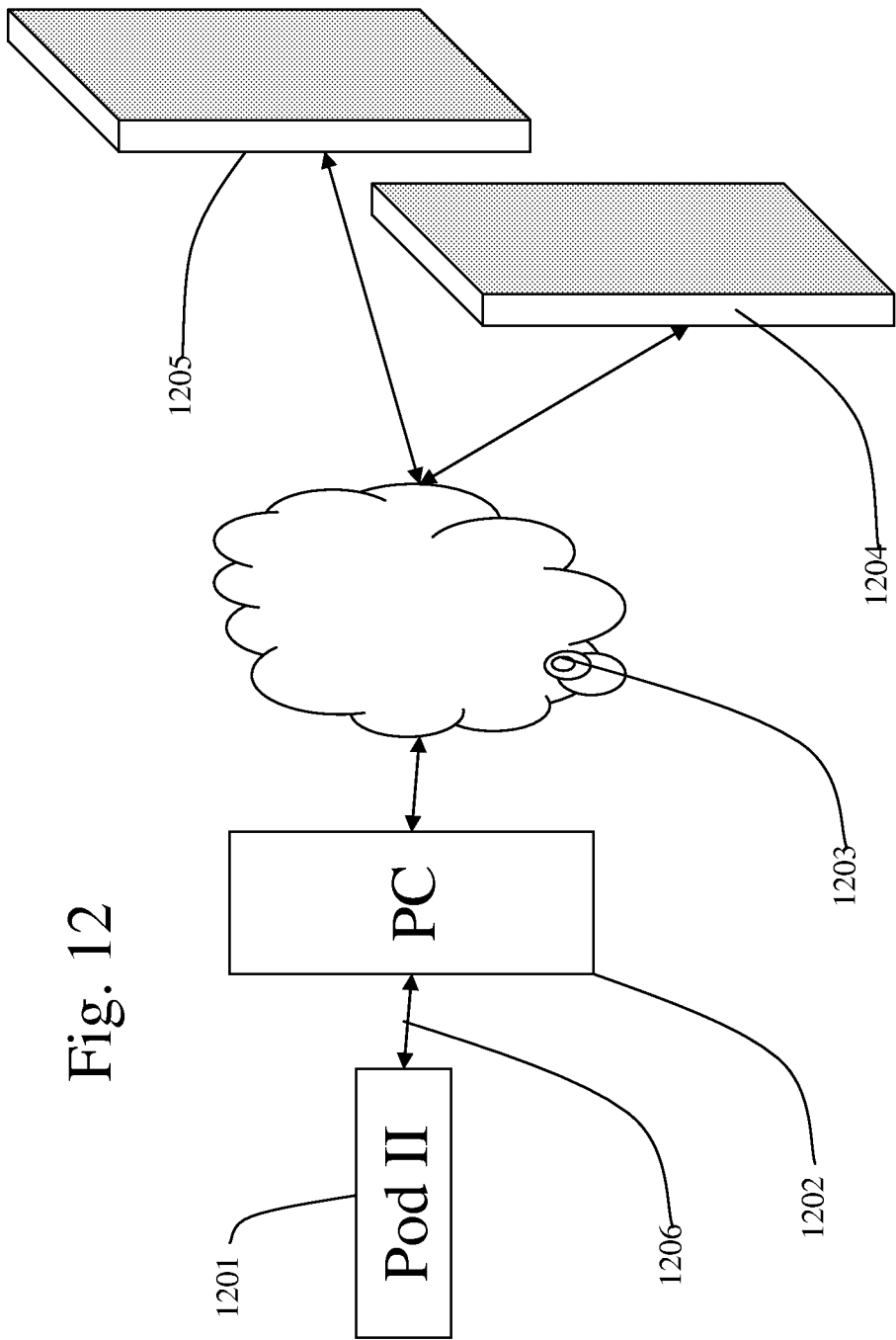

APPARATUS AND METHOD FOR OBTAINING AN IDENTIFICATION OF DRUGS FOR ENHANCED SAFETY

RELATED APPLICATIONS

This application claims the benefit of Provisional Applications Nos. 60/798,278 and 60/798,279, both filed May 6, 2006.

FIELD OF THE INVENTION

The invention pertains to an apparatus and method for obtaining characteristics of a drug, and identifying the drug. The invention may be used in conjunction with patient care associated with a prescribed drug regimen.

BACKGROUND OF THE INVENTION

Drugs are effective in treating a wide range of diseases and medical conditions. They are designed to be consumed according to a defined protocol, which includes dosing and timing. Demand for prescription drugs is growing at a rate that exceeds the capacity and numbers of licensed pharmacists. Currently more than 200 million prescriptions are filled in the US alone every week. The number of prescriptions filled between 2000 and 2005 increased roughly by 41%, while the number of retail pharmacists increased roughly by 4.5%.

However, there are a few major problems associated with prescribed and non prescribed drugs, which create a safety risk or reduced efficacy:
1. Drug—drug interactions which occur when actually consuming the drugs
2. Medication errors made by physicians
3. Non compliance and non-adherence by patients
4. Vending errors by pharmacists
5. Drug counterfeit Errors can be made in any stage of the drug cascade: manufacturing, prescribing, dispensing and consumption. They can occur at the manufacturing site, in hospitals, pharmacies, community clinics and at home. Two in-patient studies, one in adults and one in pediatrics, have found that about half of medication errors occur at the stage of drug ordering, and direct observation studies have indicated that many errors also occur at the administration stage.

The purpose of the invention described herein is to assist patients and people who consume medications to considerably reduce the risk associated with these factors.

1. Drug—Drug Interactions:

All drugs affect multiple organs and many systems, and have different mechanisms of absorption, distribution metabolism and elimination. However, many, if not most, individuals take more than one drug at a time. Once a drug is consumed, it may alter one or more of the mechanism of action of another drug causing a reduction of efficacy or a toxic effect.

While clinicians are in general familiar with the concept of cross activities of drugs, which are mentioned in the summary of product characteristics (SmPC) and prescribing information (PI), in many cases they are unaware of specific potential interactions while prescribing a drug for one of the following reasons: The clinician is prescribing the drug only in rare cases, the drug is new on the market, the patient did not disclose all drugs he/she is taking (or was not asked about them), personal habits are not disclosed (dietary, alcohol, smoking, etc.) or the clinician or the pharmacist is not familiar with many of the possible combinations of drug interactions 2. Medication Errors Medication errors are errors in the processes of ordering, transcribing, dispensing, administering, or monitoring drugs, irrespective of the outcome (i.e. injury to the patient).

3. Non-Compliance and Non-Adherence

Non-compliance and non-adherence errors are made by the patient. The principal types of non-compliance errors are: missing a dose, incorrect drug, incorrect frequency of administration, or completely stop taking the drug 4. Vending Errors This type of errors occurs when drugs are sold by a pharmacist to the patient. Typically, these errors occur due to similar names or similar packages of drugs. A high work load on pharmacists also contributes to the error rate.

5. Drug Counterfeit

This is a growing issue where a look-alike drug, which may contain an inert or a different material, is sold on the market as if it were the original drug. The danger here is that the patient will not get the benefits of the proper drug, at all.

SUMMARY OF THE INVENTION

The present invention refers to a system which performs identification of a drug before it is taken by a user, comparing it to known drugs, verifying whether adverse drug interactions can exist, and providing an alert in dangerous situations. The product may also include a unit for reminding a user to take the drug at the appropriate time.

For purposes of the present invention, the term "drugs" is used to include prescription drugs and non-prescription drugs (also known as Over the Counter (OTC) drugs), medications and preventive drugs.

In its most general form, the product includes an identification module based on analysis of one or more physical characteristics of a drug to be identified, and a memory or database including physical characteristics of known drugs. In one embodiment of the invention, the identification module includes an image analysis of solid drugs, such as pills, tablets and capsules, for example, using light sources and at least one camera. Alternatively, there can be an RFID module to identify packaging of drugs equipped with RFID, or a barcode scanner for scanning packaging of non-solid drugs, such as syringes. In other embodiments, identification modules may be based on Near Infra-Red (NIR) technology or other technologies suitable also for liquids, powders, and emulsions.

In addition to the identification module, which, in one embodiment is integrated into the product, the product includes a processor, memory, user input and output devices, such as an LCD capable, in some embodiments, also of video display, touch screen, loudspeaker, microphone, power connector, battery backup, and a communications module, as well as data storage capacity.

The product can be of dedicated design tailored to this application, or can include a camera-equipped mobile phone capable of running software, or any other device that can link to various hardware accessories and subsystems that together are capable of performing the desired functions of the product.

Thus, the invention relates to medication errors in general, and to a device and method that can generate images or other data of medications and other drugs prior to their consumption by a patient or consumer. The device further includes communication capabilities to provide the consumer with information about drugs.

The device described herein is referred to as a "Pod". The Pod is preferably a consumer-operated device, that is preferably used by consumers to verify that the drugs they are about to take are safe for use and free of errors that are associated occasionally with taking drugs (medication errors). One aspect of a preferred Pod is to act as an intelligent reminder for taking medications, thus enhancing compliance. But this aspect is only one of several important aspects, all related to drug safety, as described above.

According to a preferred embodiment of the invention, a user has a single Pod having a hardware identification code, the Pod being associated with the user. However, it should be noted that more than a single Pod can be associated with a user and more than one user can use the same Pod. The terms "user", "consumer" and "patient" will be used in this application interchangeably. The reason for this is because drugs are taken today not only to relieve an acute disease. For example, people take cholesterol-reducing drugs without being defined as "sick". Therefore, most people who take drugs in the form of pills are potential users of the present invention. The terms "drug", "medicine" and "medication" will also be used herein interchangeably.

Preferably, according to the present invention, the Pod includes a constant communication link to a server. The server is referred herein as a "Pod Server". However, a Pod may also operate as a "stand-alone", for example, in cases where a link to a Pod Server is not available at a particular moment.

According to another preferred embodiment of the present invention, there is provided a drug recognition apparatus which includes a drug identifier, a communication link, and a controller. The drug identifier preferably includes a drug path along which a drug moves during the identification process. Images and/or other characteristics of the drug are collected and transmitted via the communication link, in a raw or processed format to a remote server, which identifies the drug. The apparatus then receives a return message that confirms or denies the drug compatibility with a pre-selected drug regimen. In other preferred embodiments, the apparatus may perform certain identification operations, or even complete image analysis, autonomously.

The invention described herein is a comprehensive system which:
  Identifies each tablet pill or drug, at the final target point, just before consumption,
  Is applicable to all drugs, in any form or shape
  Does not require any preparation or modification in the production line or packaging of the drug
  Does not require pharmacists' time, intervention or any modification at point of vending
  Is easy to use
  Evaluates in real time any patient sensitivities or possible drug interactions in accordance with a patient's clinical information
  Communicates back with the patient and/or his/her care giver
  Alerts a patient and/or care provider regarding any deviation from the planned drug schedule
  Enhances economics of drug use
  Collects detailed information about the exact ways users take drugs, together with exact identification of each drug taken. Thus, this invention may assist drug safety authorities (such as the FDA) in evaluating benefits and hazards of new drugs after the drug has been released for marketing—contributing to public health and safety.

BRIEF DESCRIPTION OF THE DRAWINGS

The present invention will be further understood and appreciated from the following detailed description taken in conjunction with the drawings in which:

FIG. 12 is a schematic illustration of a system according to an alternative embodiment of the invention.

DETAILED DESCRIPTION OF THE INVENTION

The present invention relates to a system for performing identification of a drug before it is taken by a user, comparing it to known drugs, verifying whether the user has a sensitivity to the drug or an adverse drug interaction could occur in accordance with the user's clinical information, and providing an indication of compatibility to the user.

Figure 1:
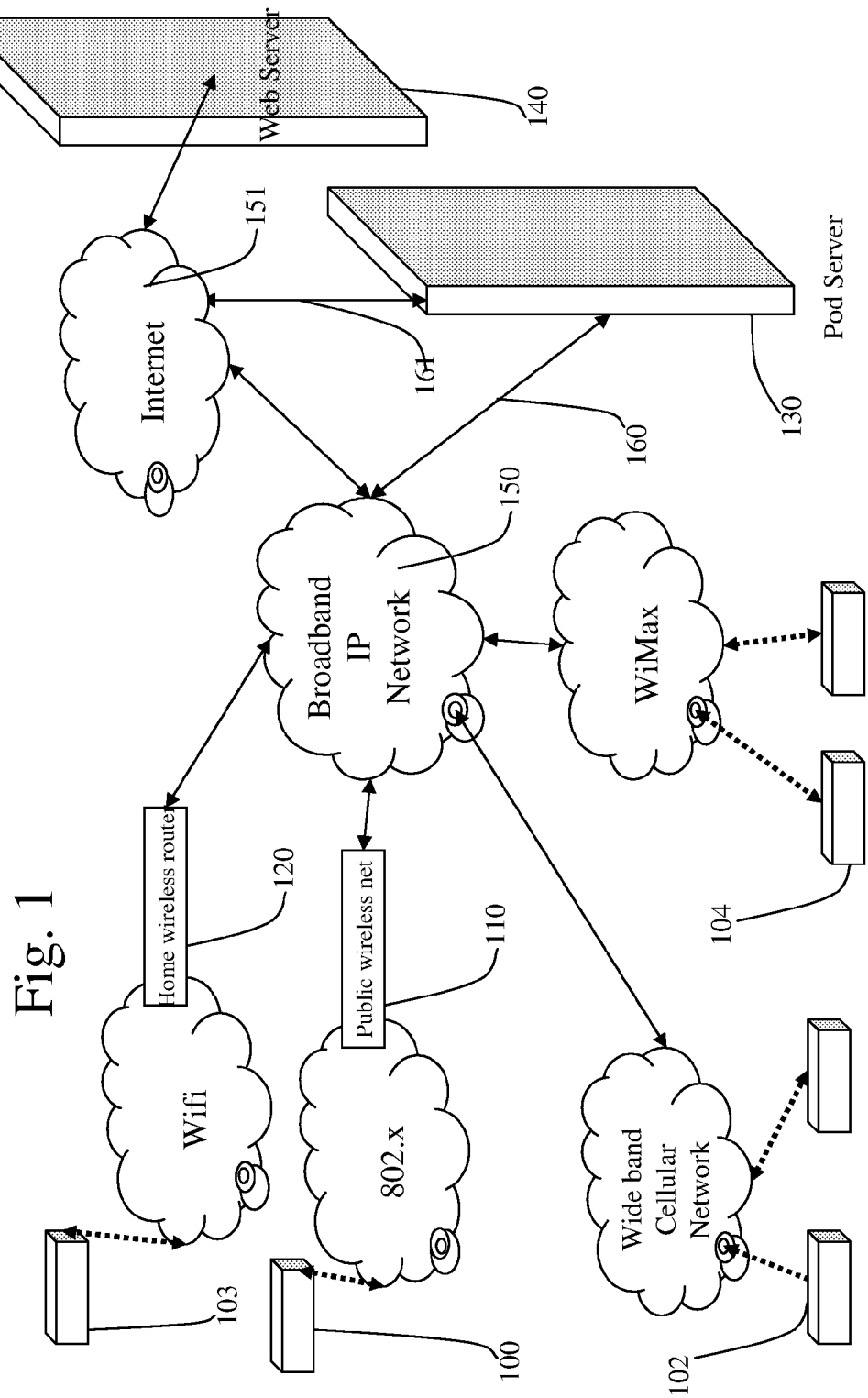
FIG. 1 illustrates the overall design of the system according to one preferred embodiment of the invention.

FIG. 1 illustrates a system architecture overview and several possible implementations of preferred embodiments of the invention. Pod 100 establishes connection to a server via a data link. According to a preferred embodiment, Pod 100 is connected to a wireless network, for example a 802.11n wireless IP network, and via a router 110 to a backbone broadband IP network 150. From the IP network 150, data is exchanged between Pod 100 and Pod Server 130. The data can be routed either via public internet 151, or via a private network or a private peering arrangement 160.

Once turned on, Pod 100 searches for a network to join. When a connection to the network is established, Pod 100 sends registration information to Pod server 130 via the network. The Pod server may be identified by a pre-set DNS name or pre-set global IP address, already stored within each Pod.

According to one embodiment of the invention, Pod 103 is located at the user's home, and connected to Pod Server 130 via a home network by known data networking links, in a similar manner to that in which a common Personal Computer (PC) communicates with servers over the Internet.

According to one embodiment of the invention, a Pod 102 can use cellular IP communications capabilities and protocols, such as GPRS, to connect to Pod Server 130, and a Pod 104 can use a wide-area wireless broadband network, such as WiMAX for connecting to the Pod server. According to an alternative embodiment of the invention, the Pod can also operate as a "stand-alone" device with its own internal memory and analysis unit. According to this embodiment, the memory may need to be updated periodically.

Pod Server 130 is connected to Internet 151 or to IP network 150 via broadband links 161 or 160, respectively. In order to optimize the solution for traffic originating from multiple Pods, or for geographic constraints, multiple Pod Servers can be used. Optionally, a load balancer, a firewall and other known means (not shown) that are utilized by web sites to balance traffic and protect against hackers' attacks that are used by Internet server centers, can be used to optimize data flow to and from the Pods.

The Pod includes at least one sensor for sensing and recording selected characteristics of a drug to be identified. The recorded characteristics are transferred for analysis for compatibility with a pre-selected drug regimen. The drug regimen includes all drugs, prescribed and not prescribed, food supplements, vitamins, and the like, taken by a person, including dosage and timing, and preferably includes an indication of allergies or sensitivities to any drugs or food supplements to be used during drug analysis. The analyzed data of the recorded characteristics is received in the Pod, which includes a display for displaying the received data. It will be appreciated that the display can include a visual, audible, or any other display elements. According to one preferred embodiment, the Pod also includes a housing defining a sensing area for receiving a drug to be identified, and the sensors are mounted in the housing. According to one embodiment of the invention, the Pod also includes an analysis module mounted in the housing and including a medical database storing selected characteristics of as many drugs as possible, and a processor for comparing the sensed characteristics of the drug to be identified with characteristics of the drugs in the database, so as to provide an indication of the compatibility of the drug. The processor may also be enabled to provide an indication of potential drug interactions.

Figure 2:
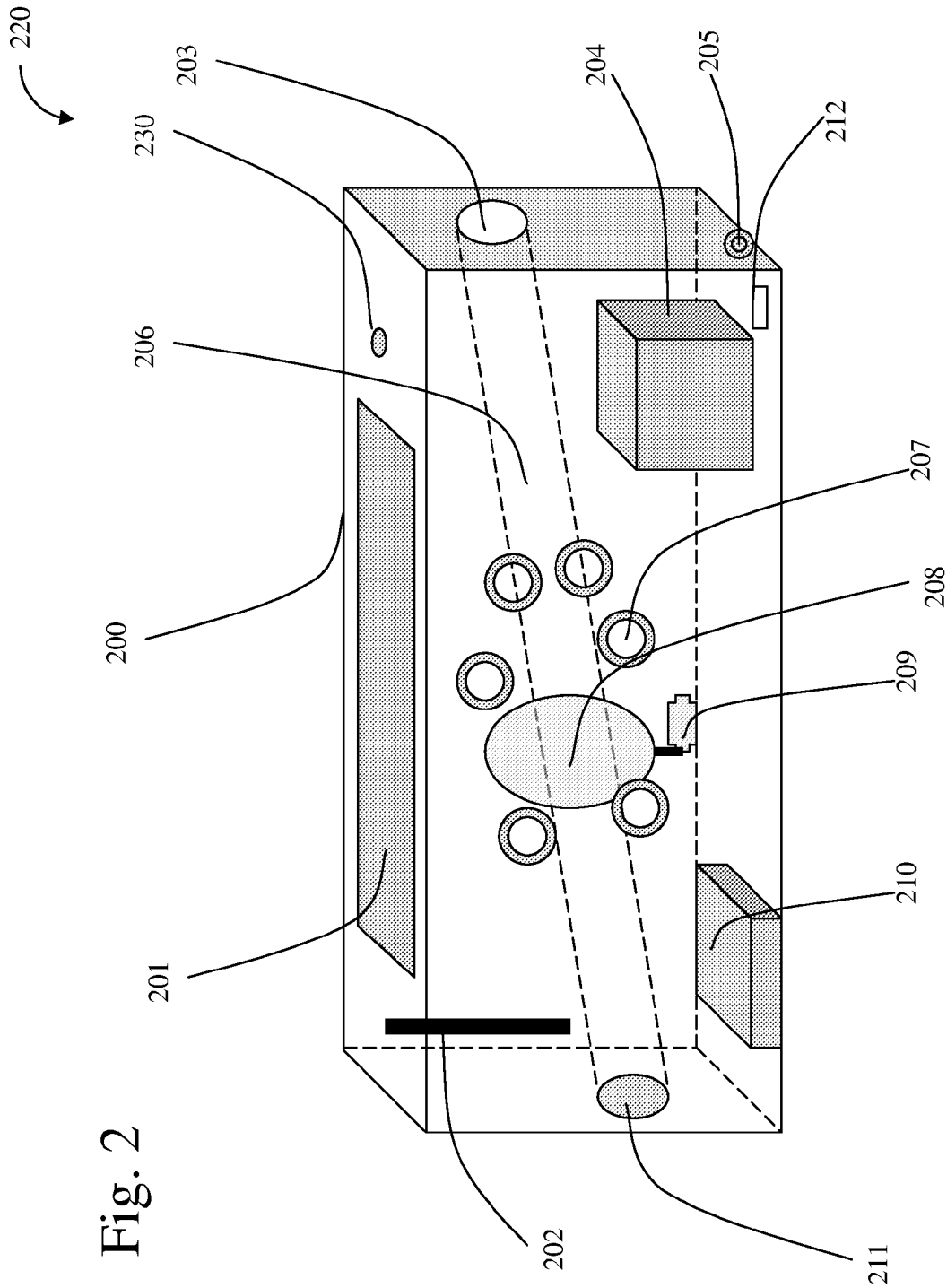
FIG. 2 illustrates the overall structure of a Pod, according to one embodiment of the invention.

FIG. 2 illustrates a Pod 220 according to a preferred embodiment of the invention. In this embodiment, the sensors include devices for capturing images of the exterior of the drug so as to permit analysis of size, color, markings, etc. Pod 220 includes a housing 200, at least one, and preferably a plurality of cameras 207, drug retaining elements, here shown as a gating element 208 and an associated gating motor 209. Pod 220 further includes a drug path 206 having at a first end a drug entry opening 203, and at a second end a drug exit 211, a power connector 205, an electronics and software module 204, a battery 210, and a display 201. Module 204 may include discrete electronics, such as hard wired circuitry, or according to a preferred embodiment, a controller controlled by software, and can further include circuitry for power management, control, etc. It is appreciated by those skilled in the art that, according to preferred embodiments of the present invention, module 204 may include communication link capabilities provided by hardware, software or a combination of both. Such a communication link can be provided by a module which is completely or partially separated from module 204.

According to a preferred embodiment, the user introduces a drug to Pod 220 through drug entry opening 203. Alternatively, Pod 220 may be connected to a drug dispenser which, automatically or when triggered by the user, dispenses a pill or pills into opening 203. The pill moves along the drug path 206 to an area for sensing characteristics. According to this embodiment, the pill is retained in the sensing area by gating element 208, which is preferably a revolving gate formed of glass, or other transparent material. Camera 207 takes a snapshot or several snapshots of the pill from one or more shooting angles. Camera 207 is shown in this embodiment as a single camera, however, preferably more than one camera may be used to capture physical characteristics of the pill from all angles. Camera 207 captures images of the pill through transparent gate element 208. It will be appreciated that camera 207 can comprise image sensors that are sensitive to the visible spectrum, for example color RGB (Red-Green-Blue) cameras which yield a color image. Alternatively, camera 207 can comprise a camera having image sensors, filters and lighting elements that produce images in the non-visible spectrum, such as near-infra-red images, which are not visible to the human eye. Infra red imaging provides an analysis of the drug's coating composition, enabling identification of the drug and also detection of counterfeit drugs. According to a preferred embodiment, only a single NIR camera is used, since NIR absorbance is a property of the surface coating of the pill and it can be assumed that the surface is uniformly coated. A camera such as Sony XCD-X710 monochrome CCD camera, augmented with an NIR pass filter may be used. A monochrome CCD has some sensitivity to NIR up to about 1100 nm. The combination of a camera and a filter (such as IR filter Hoya RM-90 available from Edmund Optics, N.J., USA) is sensitive to spectral band of 850 to 1100 nm. Alternatively, a special NIR CCD camera sensitive to wavelengths of 1460-1650 nm may be used. An example for such camera is provided by Edmund Optics, N.J., USA, catalog number NT56-567. These cameras, and the special NIR camera may output analog video signal and thus, may require a capture board (such as PCI-1405 made by National Instruments, USA) for digitization. (It will be appreciated that other cameras may have a digital interface to embedded computer systems, such as IEEE 1394.) The NIR camera should be positioned in a way not to interfere with the color cameras.

Optionally, a weight sensor may be utilized to weigh the pill, thus adding an additional parameter which will aids in identifying the pill.

Gating motor 209, or a linear actuator or any other suitable element, can revolve gating element 208, to permit the pill to continue its passage along drug path 206 and get to the other end of the Pod at exit point 211. Clearly, the specific activation of the gating mechanism will depend on the structure used and will be a technical choice clear to the skilled technician.

In a preferred embodiment, all electronics, which preferably includes a programmable microprocessor, motor driver, camera controllers, memory and communication software, is located in the electronics and software module 204. In another embodiment of the invention, these functions may be performed by a cellular telephone handset that is coupled to the Pod, as via a cable. Power may be fed via power connector 205. According to one embodiment of the invention, at times when power is not available, battery 210 can provide power.

The Pod is coupled to a wireless communication network via antenna 202 that may be internal to the Pod or telescoping outwards, as needed. According to one embodiment of the invention, a display 201 provides feedback to the user. Such feedback can be, for example, the identification of the drug and additional information about that particular drug. This information can be transmitted to the Pod by the Pod Server 130 from FIG. 1. According to another embodiment of the invention, display 201 can be a touch-screen, that enables user's input for set-up or for placing orders.

According to another preferred embodiment of the invention, screen 201 has a capability to display video. The video may be received from the Pod Server as compressed video over IP protocol, such as MPEG4, for display on display 201. The video content can provide information about the use of drugs, also known as informational video. The video can also contain footage of a drug expert or technical support personnel that help the user to resolve drug-related and technical issues. According to another embodiment of the invention, Pod 220 has a video output connector that permits the content to be displayed on a television screen. The video output connector may be wired or a wireless video may be provided, as known.

According to one embodiment of the invention, a LED 230 can also be used to provide visual feed-back to the user. For example, such feed-back can be green, if the drug is safe to take or red, if not.

In addition, according to a preferred embodiment of the invention, an optical or RFID reader 212 can be provided to read barcode or other data encoded on drug packaging, such as syringes, or other packaging for prescription or non-prescription drugs, vitamins or food supplements.

Figure 3:
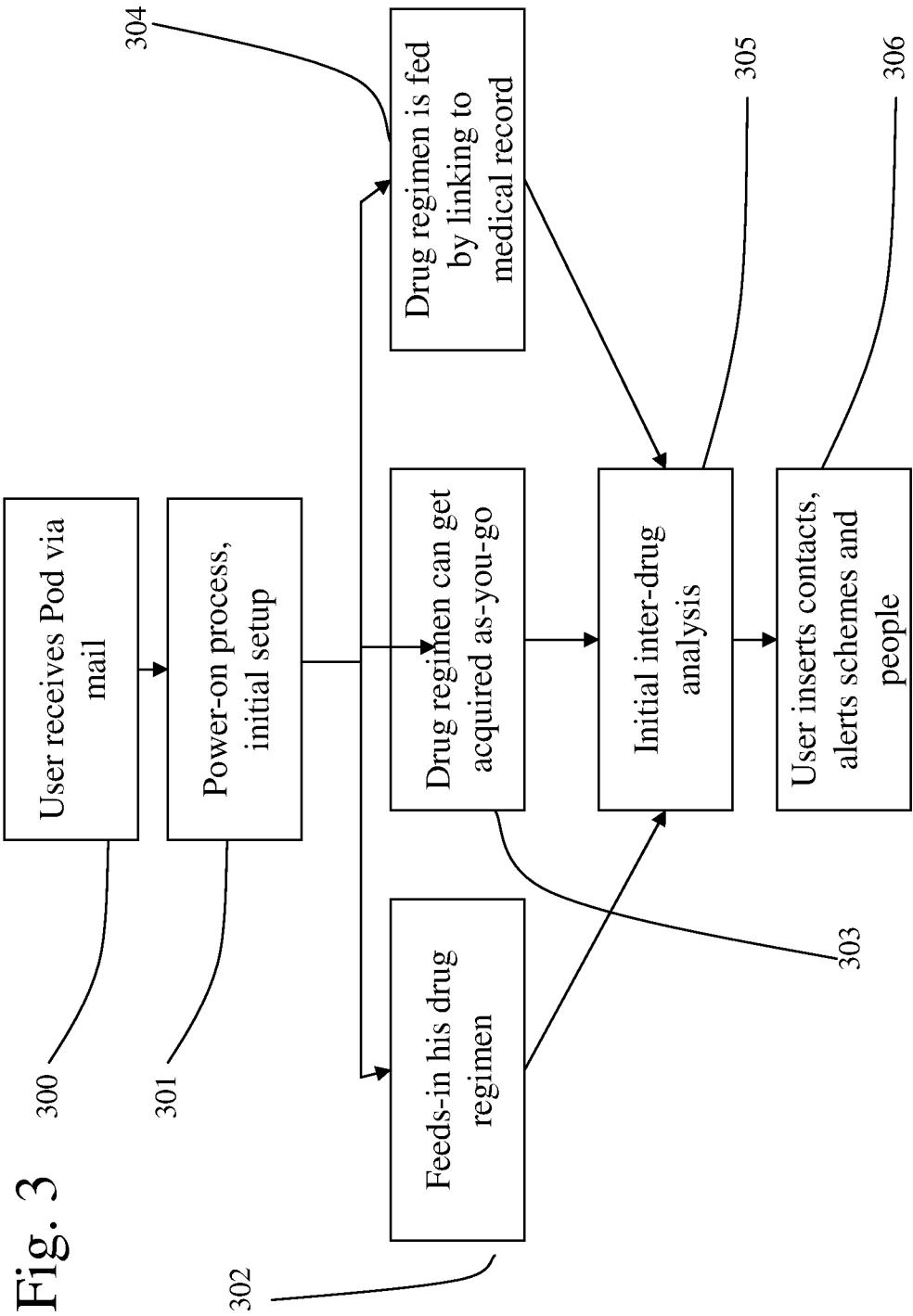
FIG. 3 is a flowchart showing how a user initiates an account and feeds data to a system as in FIG. 1.

FIG. 3 is a block diagram illustration of a preferred embodiment for a set-up process. In step 300, the user receives a Pod, such as Pod 220 in FIG. 2, e.g., via mail. Each Pod has a unique ID number, such as MAC (Media Access Control) address associated with it, and this ID preferably is associated with the user account stored in Pod Server 130 in FIG. 1, at the time of ordering. In step 301, the Pod is powered up. At this stage, initial setup parameters are fed into the Pod. These parameters may include username, password, and specify a wireless or other network to connect to, including network access keys, such as WEP (Wireless Encryption Protocol) or encryption keys or codes, as required by the particular network. Another aspect of this step is to send to the Pod, via the network, the current time and date. It is preferable that, via the IP routing tables, the Pod Server will recognize the time zone the user is in for appropriate time and date information. However, this function may also be achieved utilizing alternatives, such as reception of radio waves, manual time setting, internal clock, satellite signal, Global Positioning Technology (GPS), and the like. The time, and possibly the time zone data, may be used later to alert the user to take medications on time.

Steps 302, 303 and 304 depict three alternative steps for the entry of a user's drug regimen to the Pod Server. According to a preferred embodiment of the invention, the user can select his preferred option via the display 201 in FIG. 2 on the Pod. In step 302, the user will enter his/her regimen by using a PC (Personal Computer) connected to the Internet and, through the Internet, to Web server 140 in FIG. 1. According to another embodiment of the invention, the user may enter his/her drug regimen via the touch-screen 201 in FIG. 2, by using a virtual keyboard presented on the display.

In step 303, if the user chooses to, the drug regimen can be acquired and stored as-you-go. In this case, the user starts using the Pod. Initially, no new drug will be verified by the system, and the Pod will alert the user, or his care giver, that the user is taking the wrong drug. However, while in this mode, the user can override the warning, for example, by typing in his password. By doing this, the user instructs the system to store and memorize that particular drug as part of his regimen. In addition, the user will input the number of times per day he should take this drug.

In subsequent instances where the user must take the same kind of drugs, no warning will be provided, as the drug is already stored as part of the user's regimen. Yet another alternative is depicted in step 304, where the user's drug regimen is acquired from a computerized database. Such databases may exist with the medical insurers or with pharmacy chains or can be received from a hospital or doctor's office.

In step 305, the Pod server performs an initial drug to drug interaction analysis, in order to make sure there are no current conflicts between drugs taken by a patient. Step 305 may take place following either step 302 or 304, or, if step 303 was chosen for the introduction of the drug regimen, it may take place prior to 303 or after 303, as the user chooses. If desired, there can be a link to external databases to provide such analysis, although preferably such information is stored in the Pod server. In addition, some safety checks can be made to make sure the dosage is according to manufacturer's or prescriber's recommendations. In step 306 the user enters, via elements described in steps 302 or via the web site, details of care givers with whom the Pod Server can communicate in case an alert needs to be sent, and communication details for communication with these care givers, such as cell phone call, SMS (text message), email, instant message and the like. Step 306 can take place at any time, and is presented here in this order according to a preferred embodiment of the invention.

Figure 4:
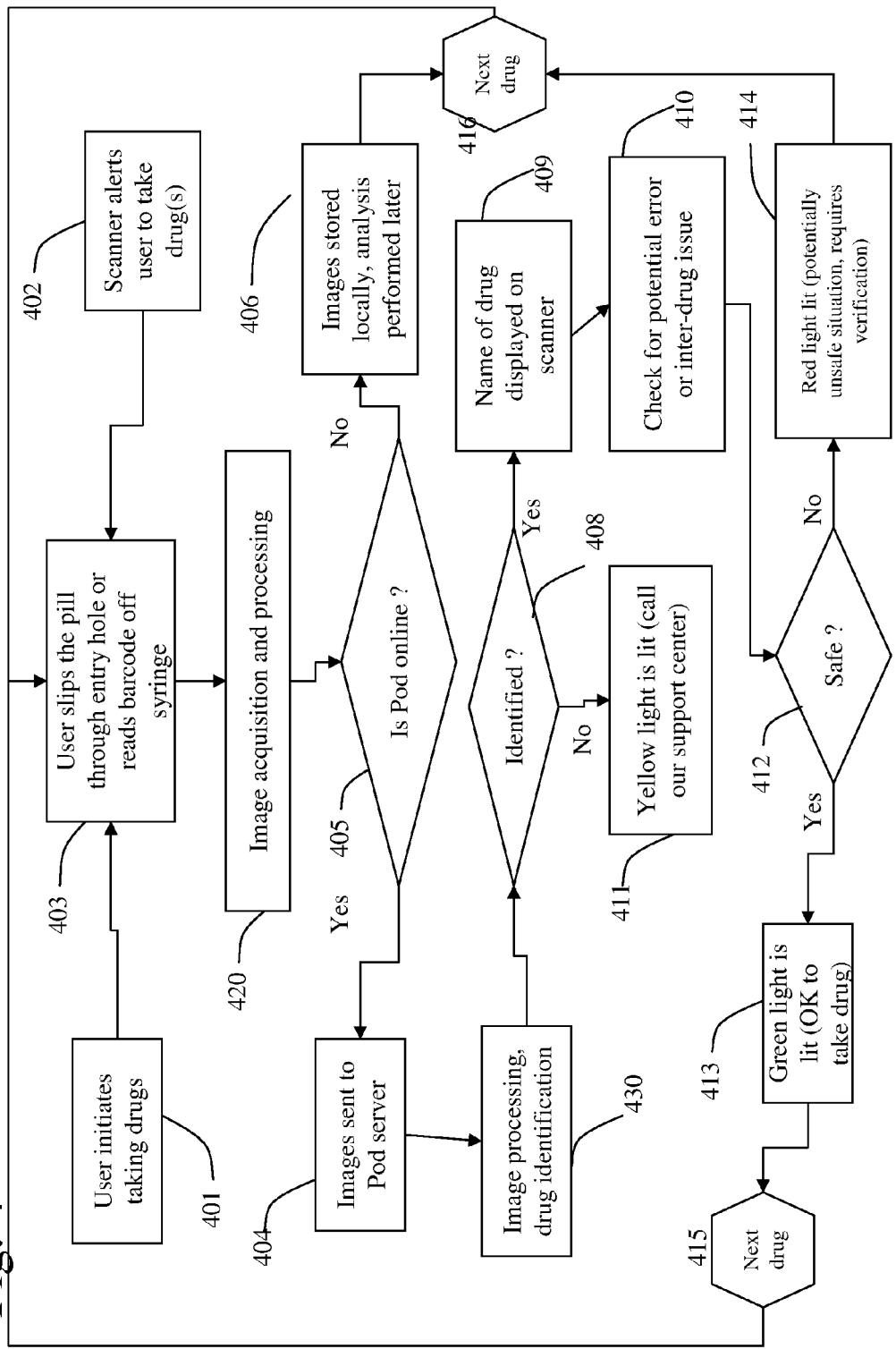
FIG. 4 is a flowchart showing how a user can use a system as in FIG. 1.

FIG. 4 shows a flow chart that, according to a preferred embodiment of the invention, is utilized each time the user takes a drug. In step 401, the user initiates the Pod for the process of analyzing drugs by selecting the "pill taking" menu on the device. According to another embodiment of the invention, the Pod is always on, and can automatically sense the presence of a drug, as by sampling one camera several times per second, or by using a drug entry sensor (not shown), various types of which exist commercially. One example of such a sensor is an IR (Infra Red) sensor.

As an alternative, in step 402, the Pod, knowing the time the user should take each drug, initiates an alert to the user, reminding him/her of the time and the exact drug that should be taken.

In step 403, the user slips in the drug through the entry opening (203 in FIG. 2), or reads bar code of a syringe or other drug packaging.

Step 420 is image acquisition and processing. The outcome of step 420 is a series of segmented or raw images. Raw images are the image data as output by the cameras. Segmented images are raw images, where image analysis has been applied, and only the object data (in our case—the portion of the image in which pill information exists) is shown. All non-relevant, or background data, is removed or is filled-out with null-values, such as 0s. The term "segmented" is used here because the image is sub-divided into two segments: the pill information, and the background information segments. The Pod now verifies that it has connectivity to the Pod Server, step 405. If it is not connected, the raw images are stored on the Pod, step 406, and will be fed to the Pod Server at a later time. Optionally, according to another embodiment of the invention, the Pod can perform image comparisons to previously stored images, or extract some features out of the raw images, in an attempt to verify there is no unexpected drug taken, even before the complete analysis is carried out.

If the Pod is connected to a Pod Server, the raw images are transmitted to the Pod Server, step 404. According to a preferred embodiment of the invention, only segmented images (described above) are transmitted. This serves to expedite the transmission process by avoiding sending background image data, thus reducing the quantity of data transmitted. In step 430, image processing and analysis takes place. According to a preferred embodiment of the invention, this takes place on the Pod Server. However, according to another embodiment of the invention, processing can be performed in the Pod itself or on an attached PC or a similar computing device. At this stage, drug identification is performed and the result is transmitted back to the Pod.

If the drug was not identified, step 408, a warning signal is delivered by the Pod, step 411, by using visual signals (for example a yellow light) or audible signals, and possibly accompanied by a suitable display that suggests the user to either try passing the drug once again through the Pod, or contact customer support. Then the user can proceed to the next drug, step 415.

If the drug was positively identified, step 408, the name, and possibly dosage, of the drug is displayed on the Pod, step 409. According to another embodiment of the invention, the Pod can use digital voice capabilities to vocalize the name, dosage and, if desired, other advice. The Pod Server now performs in-depth analysis for drug-drug interaction, step 410, compliance with the drug regimen for that user in accordance with the user's clinical information, recommendations for more cost-effective generic alternatives for subsequent purchases, and similar data. This detailed analysis is performed on the Pod server, according to a preferred embodiment of this invention; however it should be noted that the analysis can be performed on the Pod itself, or on an attached computing device, such as a PC. The in-depth analysis is done by comparing the pills the particular patient, or user is about to take, with a pre-stored drug regimen for that person, plus comparing what that patient has taken previously to known drug-drug interactions. These potentially harmful interactions can be found in commercially available drug data-bases and are updated on a regular basis by health authorities in each country, for example, the FDA in the USA.

The severity of the results is then evaluated, step 412. If the severity is high—for example, a wrong drug was detected or a potential drug-drug interaction was detected, an alarm signal is provided, step 414. This alarm signal can be any combination of light, text display or audible alarm, or any other suitable alarm. According to a preferred embodiment of the invention, a suitable text is displayed on the display of the Pod, explaining the meaning of the alarm. According to another embodiment of the invention, the Pod will not let the drug go through, by not releasing revolving gate 208 in FIG. 2, or blocking the release of the drug or drugs if the entry/exit mechanism is different. The drug, in this case, will be released only by a conscious action of the user, such as pressing a special button or selecting a special menu option. The situation described in step 414 can be resolved by either the user input, which acknowledges the error status as described, or, according to another embodiment of the invention, by contacting a support center that can release the drug by issuing a command remotely via the Pod Server. The user then can decide whether he/she should take the drug regardless, or contact a physician or pharmacist for further advice.

Once processing of a drug is completed, the Pod is ready to process the next drug, step 416. If there are no more drugs to take, the Pod resets itself back to the initial state, either automatically, for example, if it does not sense activity within a pre-determined timeout, such as 5 minutes, or, according to another embodiment of the invention, waits for a reset button or a start button to be pressed to go to the initial state.

If the drug is found to be safe, a safe indication light is lit, step 413, and the controller lets the drug exit the Pod, as by commanding motor 209 in FIG. 2 to revolve gate 208 in FIG. 2, effectively allowing the drug to roll out through drug exit 211 in FIG. 2. The user will take the drug or drugs, and move on to the next drug or to an initial state, as described.

Figure 5:
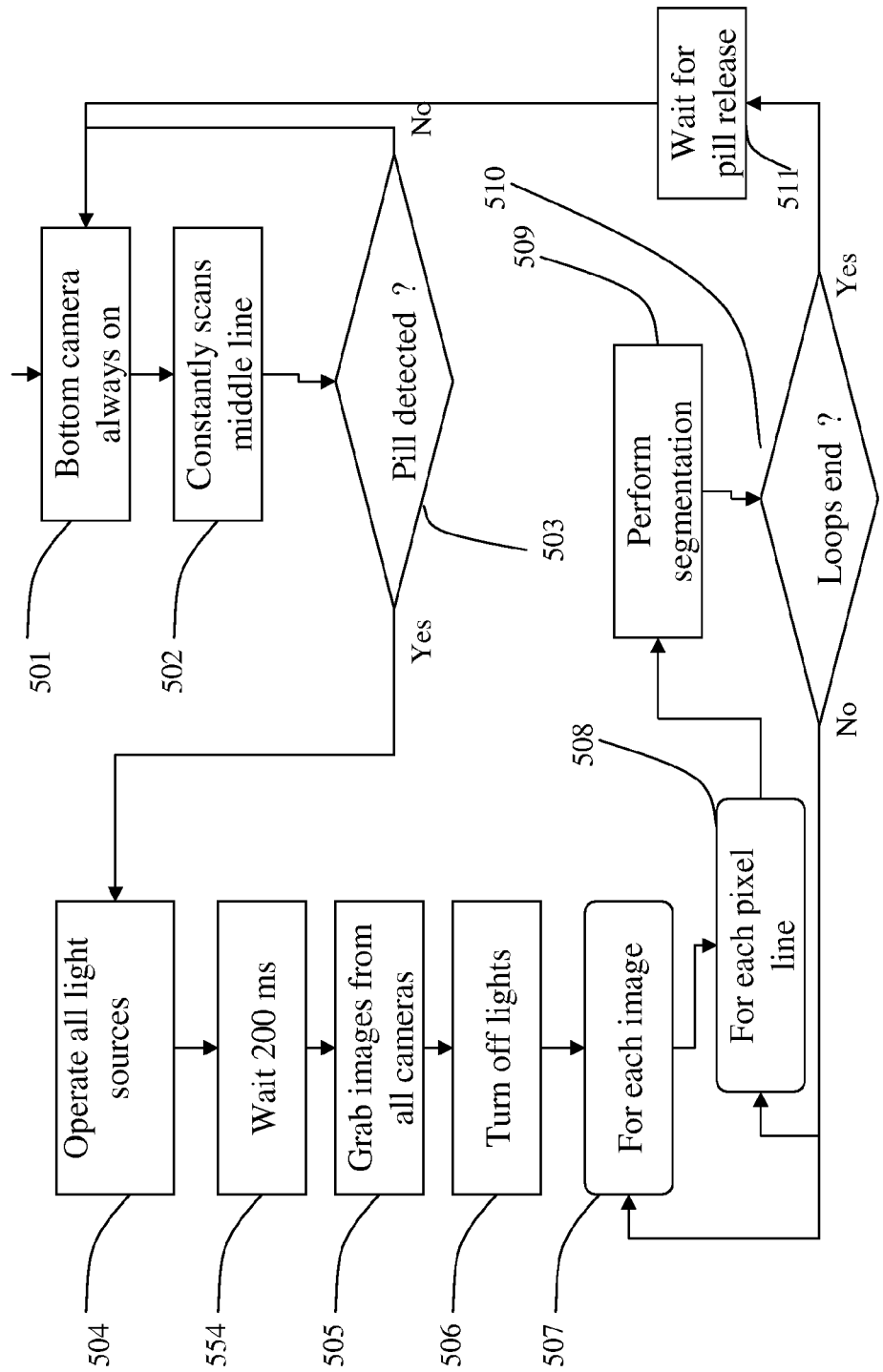
FIG. 5 is a flowchart showing the image acquisition and pre-processing according to one preferred embodiment.

FIG. 5 shows a flowchart for the image acquisition and pre-processing phase, according to one embodiment of the invention. In this phase, a drug data acquisition is performed, using one or more cameras to capture images of the drug from all required angles, strip out most of the un-needed background information and prepare the data to be transmitted to the Pod Server. Optionally, one or more cameras may use IR (Infra-Red) filters and appropriate IR lighting means, such as LED's (Light Emitting Diode) or Halogen lights (see below).

In steps 501 and 502, drug entry can be detected. In a preferred embodiment of the invention, a dim light source, that consumes very little energy, is always on, or is blinking several times per second. An example of such a light source is a Light Emitting Diode (LED). One of the cameras, typically the one that views the drug from the bottom, is operative several times per second, in synch with the light source. A simple difference algorithm can be used to detect presence of an object in the field of view. According to one embodiment of the invention, this algorithm subtracts a current image from the previous image, and if there is substantial difference between the images, concludes presence of a drug within the field of view. Many similar algorithms exist in the literature.

Once a drug is detected, all light sources are turned on, step 504. The light sources are typically LEDs that should be chosen to cover a sufficient spectrum. There may be a need to wait a short period of time until the drug is stabilized in position and until the light is stabilized, step 554. The time may be shorter or longer than 200 ms and is preferably fine-tuned according to the light source that was chosen and the mechanical design of the Pod.

Images are collected from all cameras, step 505, and are temporarily stored in memory that is embodied in the electronics and software module 204 in FIG. 2. According to a preferred embodiment of the invention, a small disk of known color or colors is placed in the field of view of each camera, in a corner that is rarely obscured by a drug. This disk or patch of colors will be used as a reference or internal standard when image analysis is performed, to determine the drug color (depicted schematically in FIG. 8). Between drugs, the light sources are preferably turned off, to preserve energy (step 506).

Steps 507, 508, 509 and 510 represent two nested loops where, for each image and for each line within each image, a simple segmentation process (partitioning the digital image into multiple regions or sets of pixels according to a selected criterion) takes place to remove most of the background pixels. According to a preferred embodiment of the invention, the images are compressed at this phase, using known image compression techniques, such as JPEG or any similar image compression method. Preferably, a typical image is expected to have a resolution of 640×480, color. These images typically can be compressed to a size between 40 to 60 KB. Thus, four images will consume, on the average, about 200 KB.

Once image cleanup and compression are completed, the drug must be released out of the Pod (step 511). This is done either automatically, as by having the Pod release the revolving gate (reference 208 in FIG. 2), effectively causing the drug to exit the Pod as described earlier, or by manual operation of the user which forces the Pod to release the drug, for example, by pressing on a special button that sends a command to the motor 209 in FIG. 2 to revolve and to move gate 208 out of the way of the drug. The Pod then waits for further drugs (step 501). Note there may be a short time delay prior to activating step 501, to allow the drug sufficient time to move out of the field of view of the camera that senses entry of a new drug.

Figure 6:
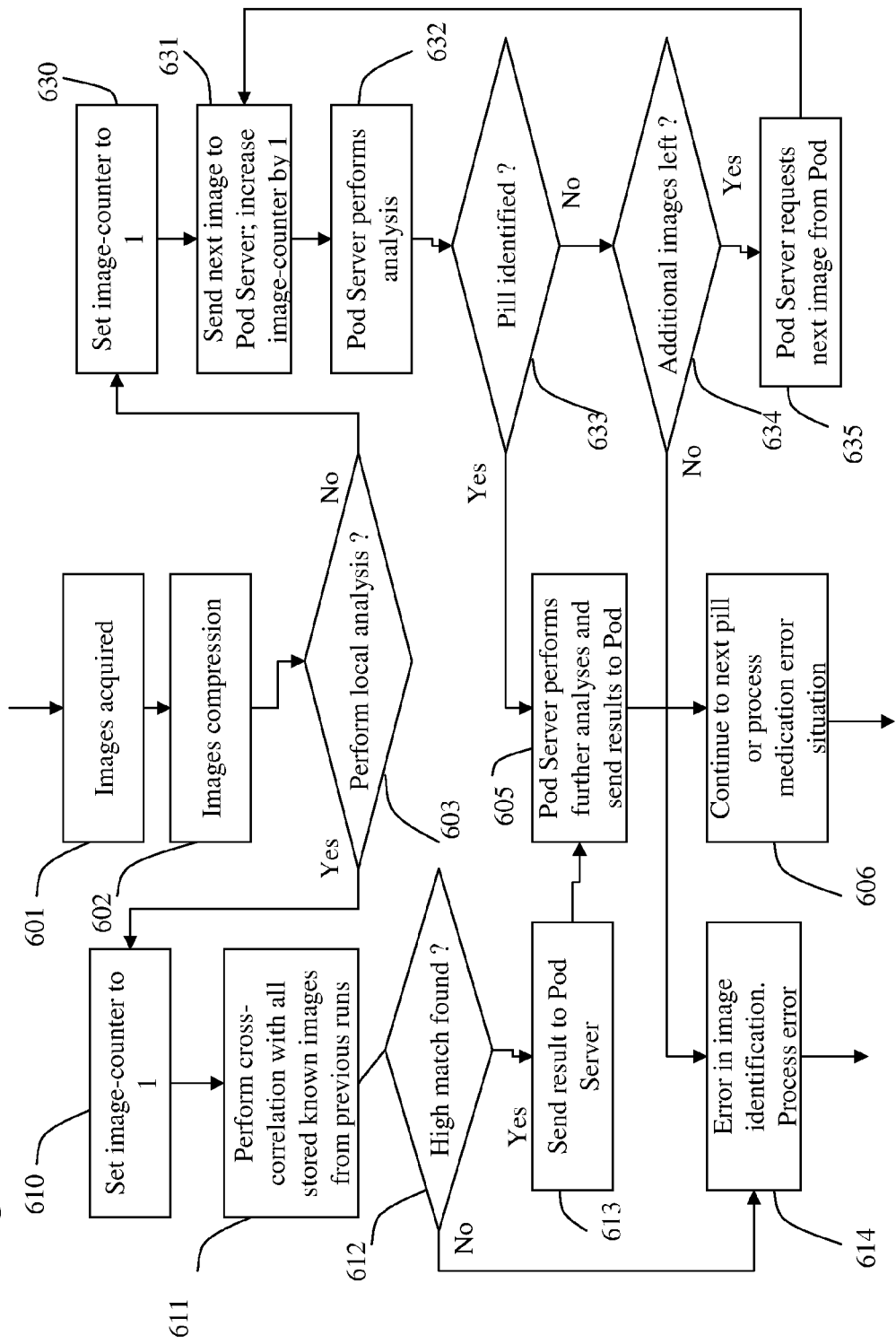
FIG. 6 is a flowchart showing an optimized image transmission process in accordance with a preferred embodiment.

FIG. 6 illustrates schematically an algorithm that is implemented in a preferred embodiment of the invention. This algorithm may replace step 404 in FIG. 4, to enable the Pod to identify a drug in less time. Broadband IP networks tend to have an upload speed that is lower than the download speed. Uploading images to the Pod server, according to a preferred embodiment of the invention, is preferable to local image analysis, as potentially more sophisticated image processing and analysis can be performed using the computing power of a server. This approach also simplifies the process of upgrading the analysis software to a newer version, as required from time to time in software-based systems, as well as updating of the database with images and other characteristics of new drugs. A drawback of this approach is the need to upload the images to the Pod server. A typical broadband upload speed today is about half to two Mbps. Although it is expected that this figure will improve over time, care should be taken to optimize image upload, in order to increase the rate of performance of the entire operation. A typical compressed image is expected to require about 50 KB. Uploading a single image of this size over the broadband connection should take close to one second. Uploading four images will take between two to four seconds, considering communication protocol overhead. Although this time is not expected to be considered as slow by users, care should be taken to minimize this time, according to a preferred embodiment of the invention.

One such an algorithm is depicted in FIG. 6, by way of example. First, in step 601, images are acquired as described above. Typically four images will be acquired, but there may be cases where six images will be needed to capture fine print on round drugs. The algorithm described herein can easily be extended by the skilled in the art to cover any number of cameras and images. In step 602, image compression is performed. Any suitable compression may be used, such as JPEG, which is a known image compression method. In step 603, there is an option to perform local analysis. Although in the preferred embodiment of the invention all analyses will be performed on the Pod Server, it may be desired to have an option for local analysis for such situations where no broadband connection exists or just to expedite routine usage of the Pod. If local analysis is performed, control proceeds to step 610. In steps 610, 611, 612, 613, and 614, the algorithm processes each image sequentially. In step 611, each image is compared to analyzed and classified images from previous runs that are stored in the Pod's memory. The comparison algorithm may include, for example, cross-correlation or normalized cross-correlation, as described in the literature. Other image analysis techniques, some of which require only minimal pre-knowledge about the anticipated structure, may be utilized. It will be clear to the skilled in the art that other algorithms may be utilized but are not desirable until such advances are made in the technological field so as to offer sufficient computing power at sufficiently low energy consumption, to make their use feasible for local drug analysis in the pod, or for allowing the pod to send only minimal data to the remote server.

If a high match to a stored image was found in step 612, the Pod sends the resulting drug code back to the Pod Server, step 613, provided there is connectivity at that time. Step 605 is optional and is performed only in cases when there is on-line connection to the Pod Server. The Pod Server performs further drug-related analysis, such as drug to drug interaction on the drugs captured. The outcome of the analysis is sent back to the Pod, typically to be displayed on the Pod's display in step 605. In case of a medication error of any type, an alarm will be provided, step 606, as described above.

If the decision in step 603 is to perform on-line image analysis that requires uploading of one or more images to the Pod Server, then step 630 is executed. Steps 630 through 635 represent a loop, in which images captured by different cameras are uploaded to the Pod Server. Inside the loop, in step 632, the Pod Server performs image processing and analysis on each image that is uploaded. There is a fair chance that the drug will be identified prior to uploading all images, and this will save both the time required to display the outcome on the Pod display, which will yield better performance and user satisfaction, and also will save processing, communication and storage resources at the Pod Server. In case the drug was identified prior to completion of the loop, in step 633, then steps 605 and 606 will take place, as described above. In case the drug was not identified yet, the system checks (step 634) to determine if there are additional images that can be uploaded to the Pod Server. If there are one or more additional such images, grabbed by different cameras, then the loop continues through step 635, in which the Pod server requests an additional image. If all images were uploaded and still there is no positive identification, special handling is provided (step 614) for the misidentification situation.

Figure 7:
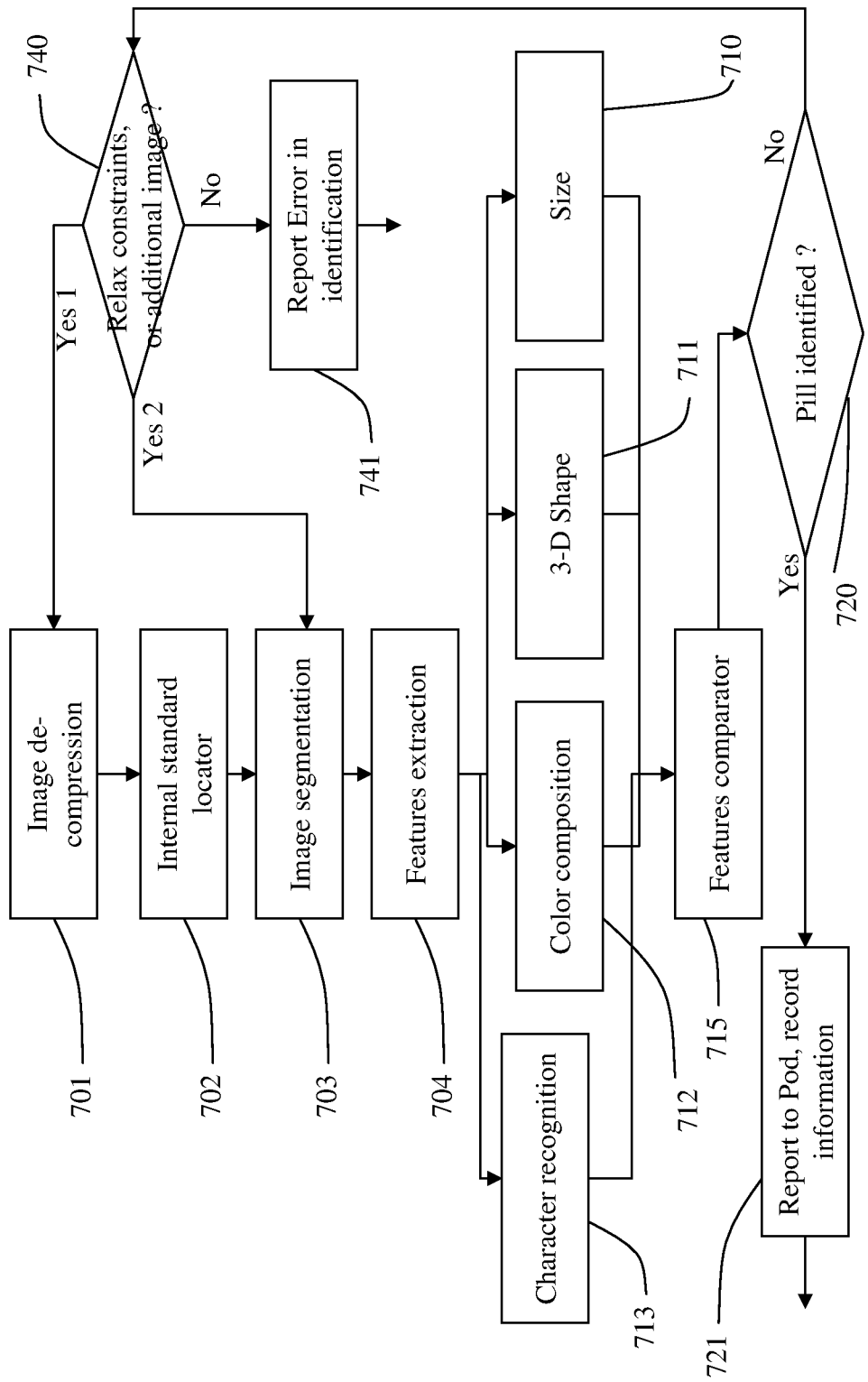
FIG. 7 is a flowchart showing an image processing algorithm according to one preferred embodiment.
Figure 8:
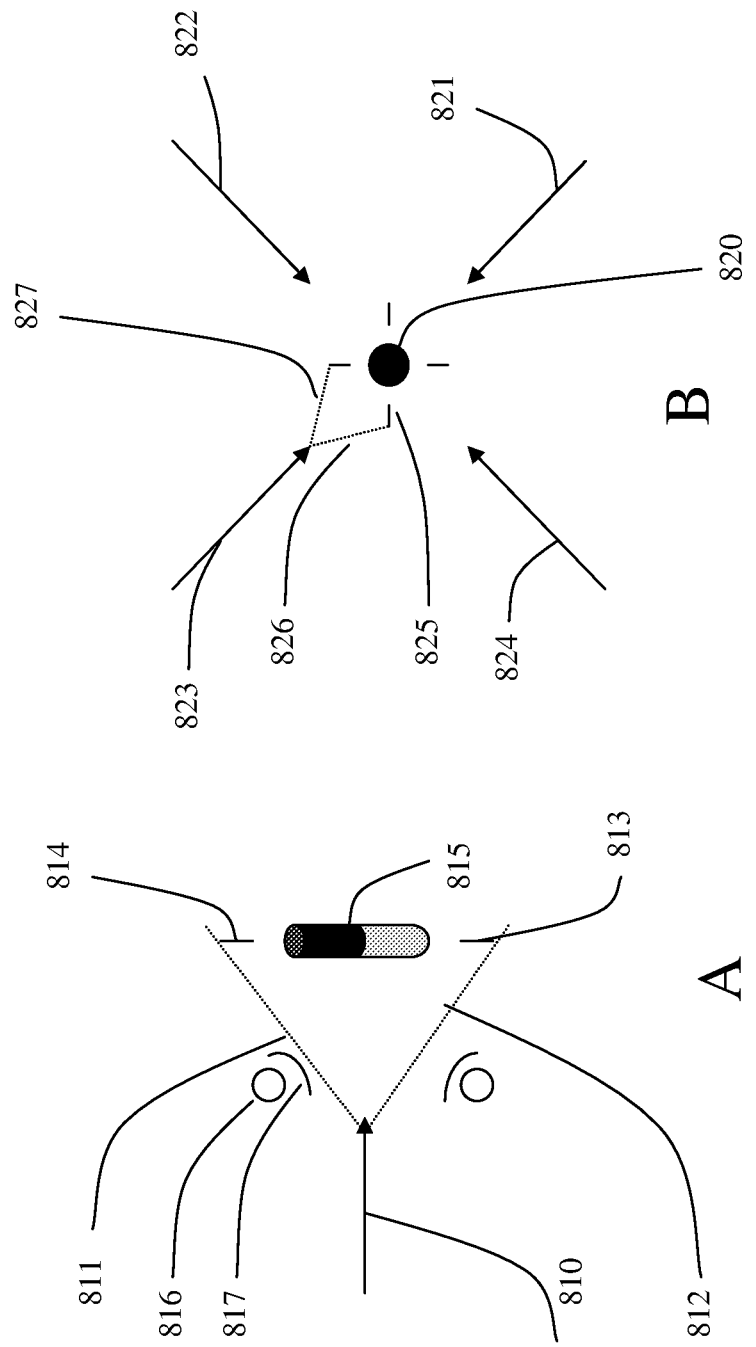
FIG. 8 is a diagram showing positioning of cameras and other elements around drugs according to one preferred embodiment.

FIG. 7 depicts an algorithm for image processing and drug identification according to a preferred embodiment of the invention. This algorithm is performed on available images until the drug is identified. There may be situations where identification cannot be obtained, and that will be treated as an error. In step 701, the image is de-compressed and is represented by an array of pixels, each pixel has its color and possibly other spectral attributes. According to one embodiment of the invention, a fixed disk of known shape and color composition is placed in the Pod and is photographed by each camera in such placement within the field of view that it would not obscure the drug. This disk is used as an internal reference and is depicted in FIG. 8. In step 702, the internal reference portion of the image is located and extracted. According to a preferred embodiment of the invention, the location of the internal reference is maintained as a rectangular shape, whose coordinates within each image are pre-determined. The area of the internal reference within each image is extracted and is saved for later calculations, and the values of the pixels that the internal reference image covered are replaced with values that are similar to the background. This is performed in order to assist the next processing phase, which is image segmentation.

In step 703, image segmentation is performed to remove the background from the images. Many image segmentation methods are described in the literature. According to a preferred embodiment of the invention, for each line of the image, there is a consecutive pixel scan that starts both from the beginning of each line, going towards the middle of the image, and from the end of each line, going towards the middle of the image in a reverse order. Each pixel value, using all color information available, is compared against a pre-set threshold. Once a pixel, or a series of at least N consecutive pixels (where N is a pre-determined and typically can be between one and four), has been found above the threshold, then a boundary point is set and recorded in an array of boundary points. It should be noted that in case the pixels in the background of the image are generally brighter than pixels belonging to the drug body, a reverse logic should be applied. That is, the criteria for establishing a boundary point should be where pixels value fall below a pre-set threshold.

In step 704, features extraction is performed. At this stage, the boundary points of the drug image are already known. Therefore, a series of algorithms can be applied in order to determine features, or properties of the drug. There are many features that can be extracted and are described in the literature. There are two hierarchies of features. The first hierarchy comprises features that are extracted from a single image that represents a single view of the drug. The second hierarchy comprises three-dimensional (or 3-D) features. These features can be calculated by considering features from the first hierarchy that were computed based on a single image or a single view. Examples of such features are volume and volumetric or 3-D shape. In this description, both features calculations will be described intermixed together, but the those skilled in the art will know that first hierarchy features need to be calculated first from all or most available views of the image and only thereafter three dimensional, or second hierarchy features can be calculated or concluded. According to a preferred embodiment of the invention, the following features are extracted. In step 710, the 2-dimesional (or silhouette) size of the drug is determined. The size may be comprised of a long axis and a short axis of the drug, and the area the largest silhouette of the drug. At a later time, when more 3-D data is available, the approximate volume may also be calculated. In step 711, the three-dimensional shape is computed. As drugs appear in a finite number of shapes, in certain cases the three-dimensional shape can be inferred by looking at only one image. For example, a 3-D shape of capsules can be determined by only looking at an image from the top. In other cases more than a single view may be needed. Reconstructing a volumetric (3D) object from its 2D images generally belong to "Shape from Silhouettes" problem and are described in the literature. The silhouettes of a 3D object such as a pill, may be calculated from the 2D images obtained from each camera with edge-detection and contour-following algorithms. These are also described in the literature. For example, the boundary of each silhouette will be represented as a 2-bit (4-way) chain code.

At this stage, the volume can be calculated at an approximate level. In step 712, the color composition is computed. Color and color combination is an important distinctive feature of drugs. For example, antibiotic capsules typically have two distinctive colors, one for the first half of the capsule and a different color for the other half. In step 713, according to a preferred embodiment of the invention, character recognition algorithm is applied to determine presence of printed information on the drug. Most drugs do have a code printed on them, or carved in them, which may assist in the identification process. According to another possible embodiment of the invention, a cross correlation algorithm can be performed using a known logo or print information or other graphical information that may be printed or carved in the drug. The FDA is maintaining a database of drugs, which includes imprint that is on or carved into drugs. This data may be used to compare against actual imprint or logo information captured. Note that in this approach, the template, or the pre-determined portion of an image that is matched against the current actual image of a drug may have to be aligned properly with the current image or several, rotated, templates may be cross-correlated with the current image.

All features are calculated, both from single views and from combining features of single views to create second hierarchy or 3-D features are fed to a features comparator in step 715. In this step, all known or measured features are compared to stored features of all known drugs. A match score of the features to each known drug is calculated. A decision making process is carried out in step 720 to verify that there is a unique match, and that the match is not ambiguous. That is—there is one and only one identification of the drug. If there is a positive match as described, the results are recorded (step 721), reported to the Pod, if needed, and control then flows to other tasks, as described previously.

Another option for a decision making process is to use Fuzzy logic rule-based identification method. A rule-based identifier may have advantages over other methods, because it is easier to extend the fuzzy classifier by adding rules or by modifying membership functions as described in the literature. A fuzzy logic identifier may be built using a set of "if-then" rules. Preferably, the rules should use clear linguistic terms, making communication with experts (pharmacologists) easier and the logic more traceable. In real-life, it is expected that the identification system will need to be updated from time to time, as new drugs enter the market. (This is also why it is preferred to couple the Pod to a central server rather than using it as a "stand along" device in the home). Updating the identifier will be achieved by adding new recognition rules. The rules may be extracted from expert knowledge (such as a pharmacologist) or learned from examining pills and figuring out differences between a new drug and existing drugs. As an example, the use of NIR as an aid for identification will be utilized in this way, because existing data-bases of drugs do not contain that information. Other rules will be derived directly by a person skilled in the art or from an existing drug data-base. These data-bases are commercially available. A concrete example of a rule may be: "IF (a region is half red AND half yellow AND form is elongated AND cross section is round AND . . . ) THEN (pill is Amoxicillin 250 mg)".

If there is no positive match, evaluation is carried out (step 740) to determine if the non-match situation is a result of poor segmentation of the current image, or a result of insufficient information, perhaps missing 3-D data. If the non-match is a result of poor segmentation (marked as "Yes 2" in FIG. 7), then segmentation parameters, such as threshold, are relaxed. Parameter relaxation is the process in which the threshold or thresholds are reduced, potentially allowing more pixels to pass thorough filters. For example, assuming not sufficient number of pixels were classified as belonging to the drug, because the algorithm assumes all drug pixels are above a certain threshold, then in a next iteration of the algorithm the threshold is reduced (or "relaxed") by a pre-determined value. Re-segmentation of the image and repetition of the process described herein are carried out (step 703). In case additional 3-D information is required (marked as "Yes 1" in FIG. 7), processing of an additional image will be carried out (step 701) to complete the 3-D information that may assist in drug identification. If the algorithm was exhausted, that is, all pictures from all angles were processed, parameters were relaxed, and still there is no match that meets the criteria for a good match, error status is reported (step 741).

FIG. 8 depicts an arrangement of cameras according to a preferred embodiment of the invention. It should be noted there are plurality of ways to arrange cameras to view a drug from all or most aspects and the actual design may vary according to resolution, optical characteristics, size and cost of the components. In addition, and as noted herein, one or more cameras may be used. In FIG. 8, "A" depicts a single camera view, while "B" depicts a spatial arrangement of four cameras. Camera 810 is shown as an arrow that represents the optical axis of the camera. Lines 811 and 812 define the optical field of camera 810. Drug 815 is located at the center of the field of view. 816 is a lighting element, such as a light emitting diode (LED) or a halogen lamp or a tip of a light guide or direct illumination or illumination via mirrors or lenses to illuminate the drug.

According to a preferred embodiment of the invention, a light reflective or light scattering element 817 is deployed, to ensure an even light distribution over the entire field of view of the camera and to prevent light reflections from the drug. Preferably, the lighting elements are positioned in such locations so that cameras that are located on the other side of the drug will not capture direct illumination from that light source. In a preferred embodiment of the invention, the light sources will be positioned behind the internal references 813 and 814 when viewed by other cameras. 813 and 814 are disks that are painted in such color combination that represents the major colors used in the drugs industry. 813 and 814 are called internal references as they possess a known color combination and can be used as a reference point for color content evaluation of the drug image. According to one embodiment of the invention the internal reference disks have four stripes: green, red, blue and black.

In FIG. 8B, 820 is an illustration of a drug to be analyzed, shown from the top. From this angle, one cannot conclude whether this is a round, small and flat drug or a capsule, similar to drug 815, but viewed from its top. Four cameras 821, 822, 823 and 824 are depicted as arrows. The arrows correspond to the main optical axis of the cameras. For camera 823, the field of view is defined by 826 and 827, which are the boundaries of the field of view. It should be noted that all other cameras preferably will have similar or identical optical characteristics, although for various reasons this may not be the case. 825 is an internal reference disk. There may be additional internal references. According to a preferred embodiment of the invention, the cameras are not all positioned on a single plane, but are rather positioned at different heights from the drug 820, a structure that resembles a tetrahedron. This arrangement optimizes coverage of all surfaces of the drug 820 by the cameras and prevents lighting interference between cameras.

Figure 9:
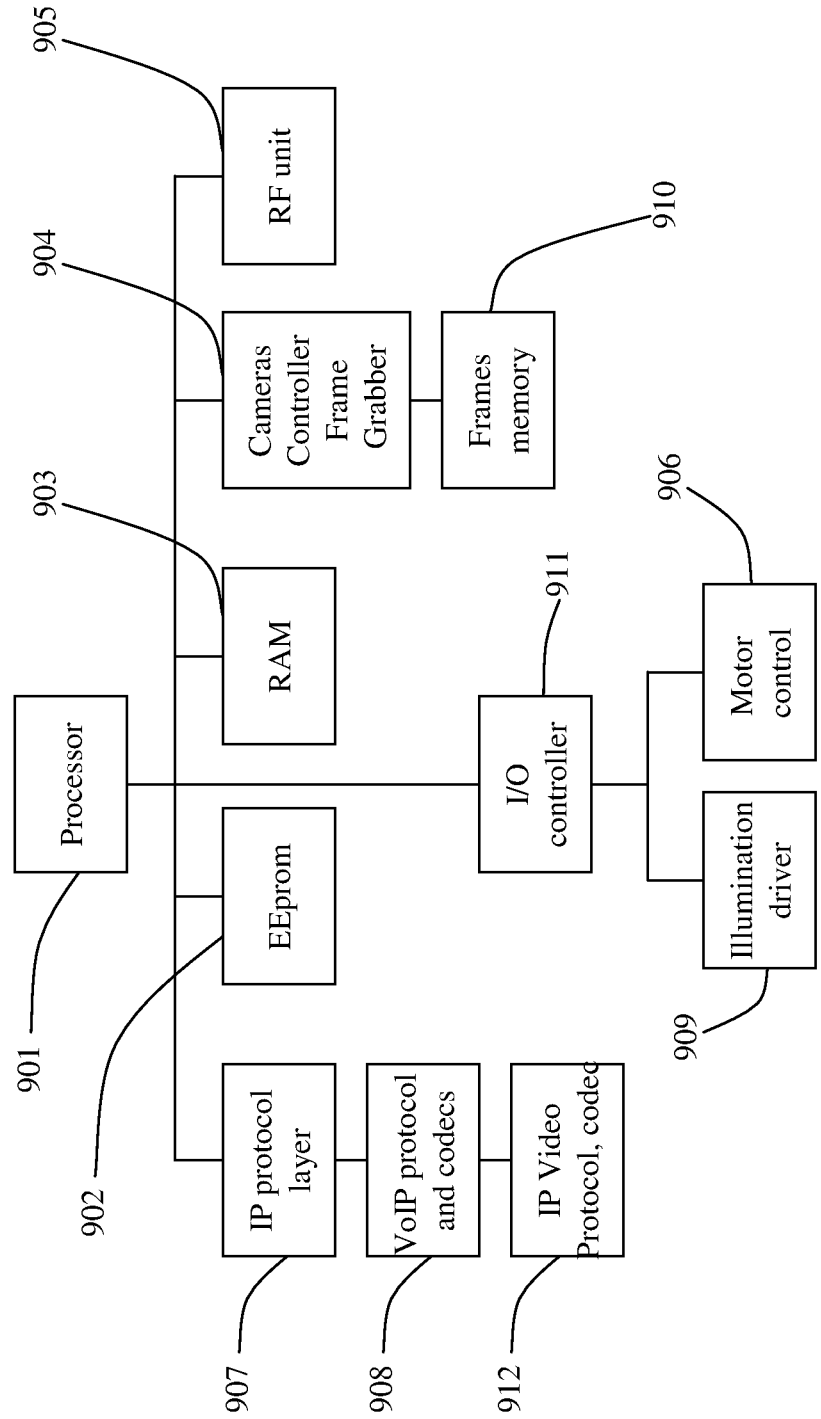
FIG. 9 is a simplified diagram showing the primary electronics and software building blocks according to one embodiment of the invention

FIG. 9 depicts a simplified block diagram of a Pod according to a preferred embodiment of the invention. Most of the functions described herein can be implemented as software modules running on a microprocessor or a microcontroller, or implemented as electronic circuitry, whether commercially available or custom-made, using known techniques such as Programmable Gate Arrays (PGA) or Application Specific Integrated Circuits (ASIC). According to a preferred embodiment of the invention, microprocessor 901 is used to control the entire function of the Pod.

Alternatively, there may be a plurality of microprocessors deployed, each performing specific tasks. For example, one processor can perform all image related functions, while another may perform all user-interface and user-interaction related functions. An example of a commercially available processor is SB-X255 single board computer, by CompuLab Ltd. (Malat Bldg., Technion, Haifa 32000, Israel). This single board computer also has a plurality of control functions that can be connected to the other units described herein. It will be appreciated that there are many alternatives on the market, either as pre-assembled building blocks or as single chips.

Coupled to the processor are two memory units. The non-volatile memory (such as Electrically Erasable ROM (EEPROM) or a regular ROM or a Flash ROM, and the like, collectively called programmable ROM) 902 and random access memory, RAM 903. Preferably, the capacity of ROM 902 should be sufficient to hold reference images for all drugs taken by the user. These images are typically loaded into the memory by the Pod server only after the initialization process that is performed by the user, as described. Thus, the microprocessor 901 should have capabilities to store this and other personalized information in the ROM. In addition, the ROM holds the operating system and all software. The RAM should have sufficient capacity to hold the programs, provide buffers for communication and other normal functions associated with memory. The processor further includes a plurality of input/output (I/O) functions depicted in 911, to control such I/O associated with touch screen, power, battery charging, and the like. The I/O controller further controls illumination (block 909) and motor control (block 906). A camera controller and frame grabber are represented by block 904. Controller 904 is connected to a frames memory 910. According to a preferred embodiment of the invention, memory 910 is a dual ported memory that allows access both by frame grabber 904 and by a processing element, such as processor 901. An RF unit (block 905) controls transmission through the air, for example—WiFi, WiMAX or Cellular transmission, such as GPRS or EDGE. Blocks 907, 908 and 912 represent communication functions. According to a preferred embodiment of the invention, this communication utilizes IP protocol. The communication layer carries both in-bound and out-bound data, such as images that are transmitted from the Pod to the Pod Server, as well as two-directional voice and uni-directional video.

Figure 10:
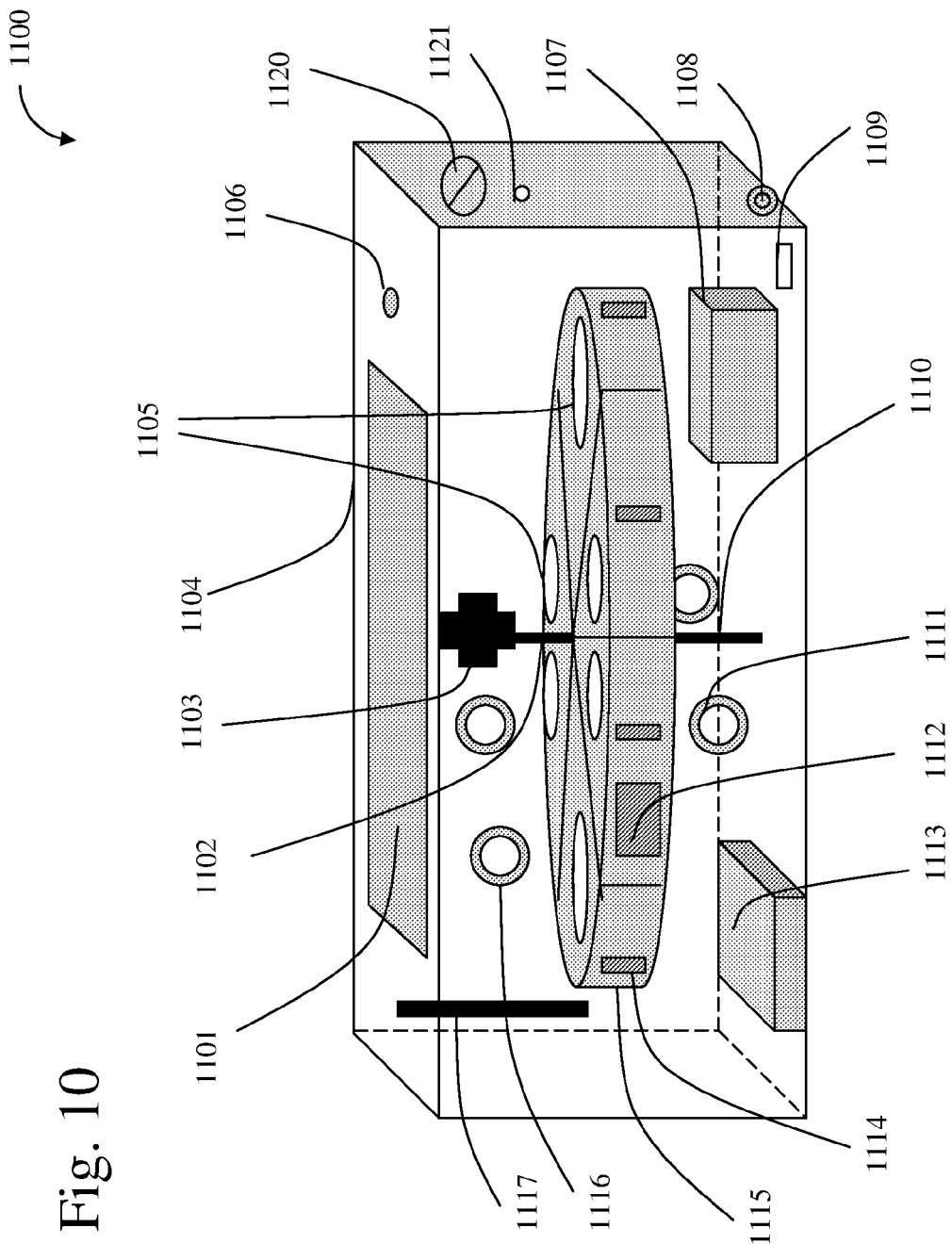
FIG. 10 illustrates a preferred embodiment of the Pod.

In FIG. 10, there is another embodiment of the Pod design. This embodiment has a replaceable central drug organizer 1115 that can be releasably coupled to Pod body 1104. There are several advantages to this approach: (a) it may be easier for people who take several drugs to place all drugs they intend to take at a time all together in an organizer. This way they can ensure nothing was left behind, and later take all drugs together, if this is more convenient for them. (b) it enables acquisition of all drugs to be taken in this instance together, further optimizing upload times and processing algorithms; (c) Preferably, each organizer 1115 can be colored differently and have a machine-readable mark 1112 identifying it as belonging to a particular member of the family, thus enabling sharing of a single Pod among family members; and (d) the movement and positioning of drugs are not dependant on physical characteristics of the drug, such as drug's roundness or drug's stickiness, which may affect the ease of drug rolling down the path, as described regarding the embodiment of FIG. 2.

According to this embodiment, Pod 1100 includes the following components: a housing 1104 with an externally viewable display 1101. The display may be one of several types, depending upon user interface design and design cost. Optionally, display 1101 may display characters only, or be of custom type that enables display of certain pre-formed icons, in addition to text. Display 1101 may display colors, display graphics, or even have touch-screen capabilities to enable user input by touching the screen. Preferably, the Pod includes a connection to a television set for better readability. Preferably, the Pod further includes an LED 1106, for alerting the user of drug errors or other conditions that may require special attention. A loudspeaker 1120 and a microphone 1121 may also be provided. According to one embodiment of the invention, Pod 1100 may include intercom-like voice capability as it is expected to be on-line at all times or most of the time. In addition, the microphone 1121 may be used to input commands to the Pod, by using speech. For speech commands, the Pod should have speech recognition hardware or software for translating spoken commands to machine instructions. Such components are commercially available for a plurality of languages. Alternatively, speech analysis, which may include speaker verification techniques for verifying the ID of the person operating the POD, may be carried out on the Pod Server.

For communication or analysis purposes, voice can be passed to and from the Pod, using VoIP or other suitable voice over data technology. For this purpose, a codec (voice encoding and decoding) software or a dedicated chip that can perform the voice function is required. An example of such a chip is BCM1190 by Broadcom, 16215 Alton Parkway, Irvine, Calif. USA 92618, but many similar chips and software packages exist on the market. The voice will reach the Pod Server and from there, using VoIP switching and routing techniques, be routed to an available agent, together with all details of the user who initiated the voice contact. If a cell phone is used as a Pod, or in connection with a Pod, then the voice or data capabilities of the cell phone may be utilized for this function. The voice contact may be provided with the user's entire drug-taking history and with images of current and possibly previous drug taking sessions. Another option is to use data. Both the user or care giver may send a data message (text message or image message or both) with either pill image or the result. According to another embodiment of the invention, voice contact may be initiated when certain error conditions are detected, such as severe potential drug-to-drug interaction or even an error in identifying a drug. The agent may then advise the user, provide technical support and perform similar tasks.

Pod 1100 further includes an electronics chamber 1107. Chamber 1107 houses various electronic components that are needed for the operations of the pod. The electronic components may be assembled in different ways, and may be disposed in various locations in Pod 1104. Pod 1100 also includes a power connector 1108. Preferably, the Pod also has a battery 113 that is activated when there is no electricity, enabling constant operation of the Pod.

Pod 1104 may also contain a bar code reader 1109, for the reading of bar codes off syringes, bar-coded drug containers, or of food additives or vitamins. It should be noted, that inspection and direct evidence of the actual drug being consumed is preferred over indirect evidence. For example, a wrong drug may be placed within a drug packaging. However, for syringes and drugs in liquid form, it may be more convenient to scan a bar code or read an RFID tag. A tag with a bar code is normally placed on syringes. Thus, it is more difficult to confuse liquid content between bottles than it is to confuse solid pills.

As described above, drug organizer 1115 can be pulled out of the Pod. Drug organizer 1115 includes special sites or cavities 1105 for receiving drugs to be analyzed. Drug organizer 1105 may include one or more cavities, depending on design considerations. In the illustrated embodiment, there are six cavities that allow for six drugs that are to be taken in a single session. According to one embodiment of the invention, drug organizer 1115 has a machine-readable marking 1112 that contains a machine readable code that identifies the drug organizer as belonging to a specific member of a family. This can enable multiple users to use a single Pod. According to one embodiment of the invention, drug organizer 1115 contains magnetic marks 1114 at the center of each drug cavity. While the drug organizer is rotated by a motor 1103, these markings signal the optimal position for a flash or strobe light and for the cameras to take a snapshot of the drug in that particular drug cavity. According to another embodiment of the invention, the magnetic mark can signal the motor 1103 to stop circulating the organizer temporarily, to enable a crisper image to be taken while the drug is not moving.

According to one embodiment of the invention, drug organizer 1115 contains a protective cover or protecting plastic leaves on the bottom (not shown). The protective cover or leaves should prevent dirt from accumulating on the bottom of the organizer, as the bottom preferably should be transparent, in order to enable circumferential imaging of the drug.

An axis 1122 having two portions 1102 and 1110 rotates drug organizer 1115. According to a preferred embodiment of the invention, axis assembly 1122 includes a flexible mechanism that enables retraction of the axis portions (1102 upward and 1110 downward), to enable smooth insertion of the organizer. Once the drug organizer is in place, axis portions 1102 and 1110 are pushed to hold and rotate the organizer. When done, these elements are retracted again to enable easy removal of the drug organizer.

Pod 1100 may further include a reader 1109 for machine-readable code that may exist on the drug or on the packaging. Examples of such codes are RFID or bar-code. An electronics and software module 1107, similar in function, construction and description to electronics and software module 204 in FIG. 2, is further included in Pod 1100, as is a battery 1113, which is similar in function and description to battery 210 in FIG. 2, and a communication antenna 1117, which is similar in construction and description to antenna 202 in FIG. 2.

1116 and 1111 indicate cameras that view drugs from all aspects. In this embodiment, four cameras are depicted. However, it should be noted that the actual number of cameras to be implemented may vary between one and six or even more, depending on practical considerations and the need to reach a certain performance level of the Pod. In another preferred embodiment of the invention, only a single camera is used to take a snapshot of all the drugs together. This embodiment may be preferred as the spatial resolution of cameras increases and prices fall. Thus, the resolution of a single camera may be sufficient for the purpose of drug identification. Likewise, two cameras may be used, one for each half of the field of view.

Figure 11:
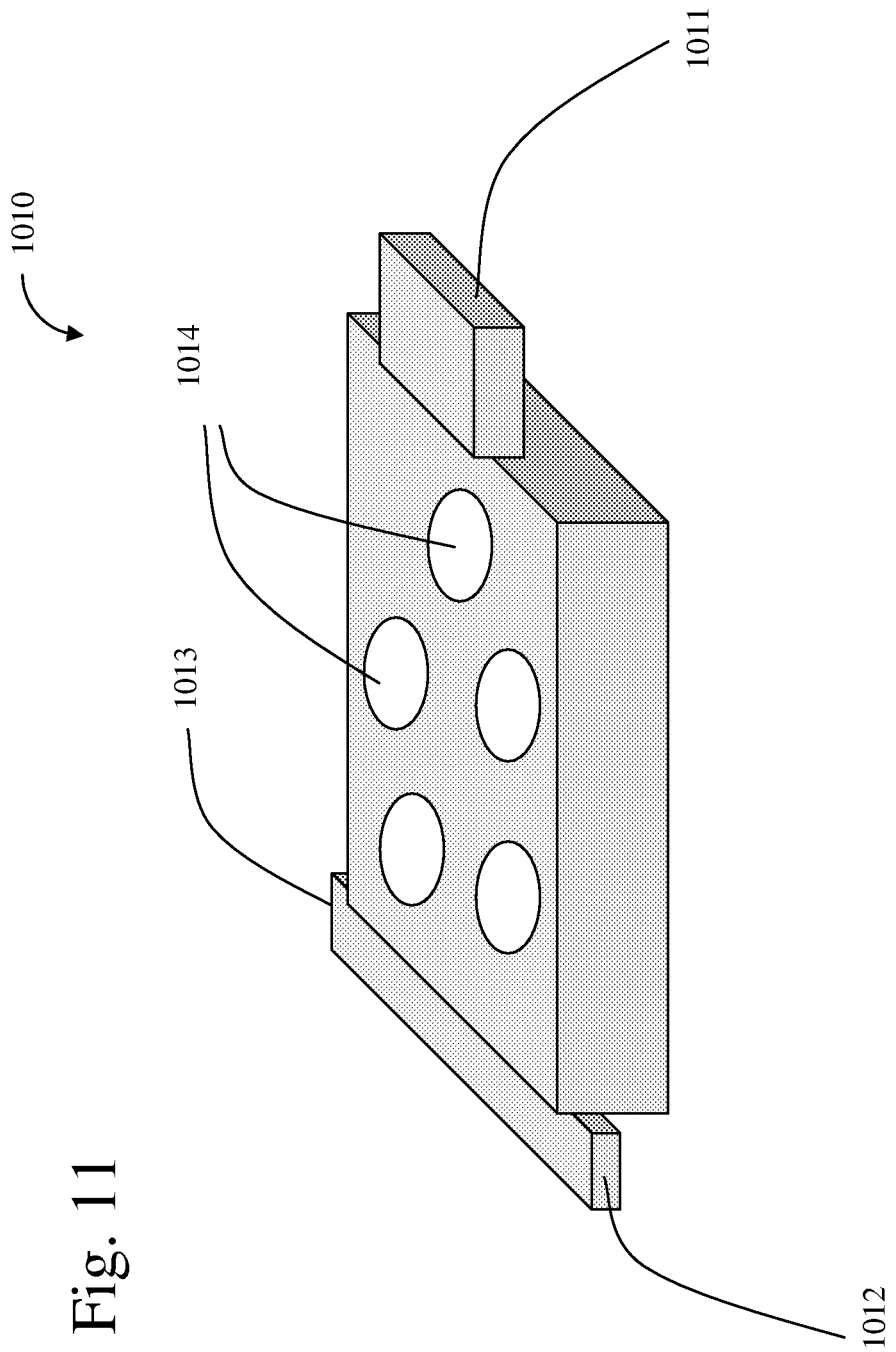
FIG. 11 illustrates a drug organizer according to one embodiment of the invention.

FIG. 11 depicts an organizer 1010 according to another embodiment of the invention. According to this embodiment, there is no need for a motor 1103 and axis assembly 1103 and 1110, as depicted in FIG. 10. Rather, the drug organizer 1010 will be inserted into the Pod, in the way a CD or DVD media is inserted into a CD/DVD player, and the drug organizer will sit within the Pod. Preferably, the drug organizer 1010 of this embodiment will have a non-symmetrical shape, such as shown in FIG. 11, forcing its insertion in a pre-determined orientation. Multiple cameras are placed across from the drug cavities 1014 and all images of all drugs from all angles will be taken simultaneously, obviating the need for mechanical movement. Organizer 1010 includes guides 1011 and 1012 that allow insertion of 1010 in only one direction. According to one embodiment, guide 1012 includes an edge 1013 that, by pressing a micro-sensor embedded in Pod 1104, signals the Pod that a drug organizer is inserted properly in the Pod.

In yet another embodiment of the invention, a cellular telephone that is equipped with a camera and software, as described above, may serve as a Pod (not shown). According to this embodiment, a cell phone handset, which is equipped with a camera (for example, a Motorola V330) will be utilized for drug identification. Accordingly, the user will take a photograph of the drug using the built-in camera in the cell phone handset. The image is sent via email (or a multi-media message MMS) to the Pod Server for analysis, and the result is sent back to the cell phone as SMS, for example. This embodiment has the advantage of being cost-effective, not requiring special equipment and relying on equipment most people already use.

According to other embodiments of the present invention, identification modules may be based on NIR technology. For example, a near-infra-red (NIR) camera and filters are utilized as an apparatus for accurate recognition of the drug and detection of counterfeiting of drugs. Only a single NIR camera is required since the NIR absorbance is a property of the surface coating of the drug and the majority (if not all) pills' surfaces are uniformly coated. As an example only: the NIR camera can be a monochrome CCD camera, such as a Sony XCD-X710 monochrome camera, augmented with a near-IR pass filter (such as Hoya RM-90 available from Edmund Optics, N.J., USA). A preferred placement for the NIR camera is on top of the chamber, in such a way as not to interfere optically with the color cameras.

FIG. 12 depicts another embodiment of the invention. According to this embodiment, the Pod may perform only a portion of the operations described above, and the processing can be carried out in a personal computer (PC) coupled to the Pod. Thus, a Pod 1201 contains the minimal elements required for the functioning of the sensors, which may bring its manufacturing cost down. Instead, or in addition, Pod 1201 is connected to a PC 1202 via any suitable link 1206. According to one embodiment of the invention, this link may be either USB or wireless Bluetooth. A possible benefit of the link to a PC is to eliminate the need for power, as power can be provided over the USB cable. Conventional PCs include the capabilities to carry out the remaining operations, such as display and user interface. According to one embodiment of the invention, PC 1202 runs appropriate software that communicates both with Pod 1201 and with Pod Server 1204 via a communication network 1203. Such communication network may be the Internet. The PC may also be connected via the Internet or a communication network 1203 to a web server 1205. According to another embodiment, the functions of the PC software may be similar to those described for the Pod Server. In this case, the databases and analysis software will be stored and run in the PC.

While the invention has been described with respect to a limited number of embodiments, it will be appreciated that many variations, modifications and other applications of the invention may be made. It will further be appreciated that the invention is not limited to what has been described hereinabove merely by way of example. Rather, the invention is limited solely by the claims which follow.

The invention claimed is:

1. A device for identifying a drug, comprising:
    at least one image sensor that senses and records an image of selected characteristics of an exterior of a drug to be identified, wherein the drug comprises a pill, a tablet, and a capsule, wherein sensed characteristics and recorded characteristics of the drug are obtained by the sensor in a visible spectrum or a non-visible spectrum, wherein the characteristics comprise at least one selected from the group of: size, color, marking, composition, volume, and shape;
    an electronics and software module that electronically transfers said sensed characteristics and recorded characteristics to an analysis unit that analyzes said sensed characteristics and said recorded characteristics to determine identity of said drug, and electronically receives from said analysis unit analyzed data of said sensed and recorded characteristics regarding the identity of said drug, wherein the module comprises at least one of hardware and software, the hardware is a POD electronic handset device that utilizes the software, the software performs a consecutive pixel scan on the image to detect a boundary point of the drug, and the electronics and software module is coupled to the image sensor;
    a display for received data and that displays the identity of said drug;
    a housing including a sensing area for receiving a drug to be identified; and
    wherein: said at least one sensor is mounted in said housing for sensing and recording selected characteristics of a drug in said sensing area.

2. The device according to claim 1, wherein said analysis unit is in said housing, and said analysis unit further comprises:
    a database of drug characteristics, wherein the drug characteristics database comprises characteristics of a plurality of drugs, said drug characteristics selected from the group of: size, color, marking, composition, volume, shape, and a combination thereof; and
    a processor for comparing said sensed characteristics to said drug characteristics in said database and for providing output data indicating the identity of said drug; and
    said device further comprises:
    a drug path in said housing having a drug entry and drug exit;
    a drug retaining element in said drug path that selectively retains said drug in said sensing area adjacent said at least one camera; and
    said electronics and software module further comprises at least one selected from the group of: a programmable microprocessor, a motor driver, a camera controller, and memory and communication software, wherein the module controls said drug retaining element and said at least one sensor.

3. A device for identifying a drug, comprising:
    at least one image sensor that senses and records an image of selected characteristics of an exterior of a drug to be identified, wherein the drug comprises a pill, a tablet, and a capsule, wherein sensed characteristics and recorded characteristics of the drug are obtained by the sensor in a visible spectrum or a non-visible spectrum, wherein the characteristics comprise at least one selected from the group of: size, color, marking, composition, volume, and shape;
    an electronics and software module that electronically transfers said sensed characteristics and recorded characteristics to an analysis unit that analyzes said sensed characteristics and said recorded characteristics to determine identity of said drug, and electronically receives from said analysis unit analyzed data of said sensed and recorded characteristics regarding the identity of said drug, wherein the module comprises at least one of hardware and software, the hardware is a POD electronic handset device that utilizes the software, the software performs a consecutive pixel scan on the image to detect a boundary point of the drug, and the electronics and software module is coupled to the image sensor;
    a display for received data and that displays the identity of said drug; and
    a drug dispenser coupled to said device that dispenses into a sensing area at least one drug to be identified.

4. The device according to claim 1, further comprising a central drug organizer, releasably coupled to said housing, that holds a plurality of drugs to be identified.

* * * * *